(12) United States Patent
Boseck et al.

(10) Patent No.: US 8,086,293 B2
(45) Date of Patent: Dec. 27, 2011

(54) CATHETER

(75) Inventors: Gary Boseck, Belmont, CA (US); Edward M. Gillis, San Jose, CA (US)

(73) Assignee: Medtronic Ablation Frontiers LLC, Minneapolis, MN (US)

(*) Notice: Subject to any disclaimer, the term of this patent is extended or adjusted under 35 U.S.C. 154(b) by 336 days.

(21) Appl. No.: 12/533,252

(22) Filed: Jul. 31, 2009

(65) Prior Publication Data

US 2010/0261989 A1 Oct. 14, 2010

Related U.S. Application Data

(60) Provisional application No. 61/169,263, filed on Apr. 14, 2009.

(51) Int. Cl.
  *A61B 5/04* (2006.01)
  *A61B 18/18* (2006.01)
  *A61N 1/00* (2006.01)
(52) U.S. Cl. .......... 600/374; 600/381; 606/41; 607/122
(58) Field of Classification Search .......... 600/372–374, 600/381; 606/32, 41; 607/122
  See application file for complete search history.

(56) References Cited

U.S. PATENT DOCUMENTS

| 5,656,029 | A | 8/1997 | Imran et al. | |
| 5,782,900 | A * | 7/1998 | de la Rama et al. | 607/122 |
| 6,024,739 | A * | 2/2000 | Ponzi et al. | 606/15 |
| 6,210,407 | B1 * | 4/2001 | Webster | 606/41 |
| 6,488,694 | B1 | 12/2002 | Lau et al. | |
| 6,755,824 | B2 * | 6/2004 | Jain et al. | 606/41 |
| 6,837,867 | B2 * | 1/2005 | Kortelling | 604/95.04 |
| 2005/0283221 | A1 | 12/2005 | Mann et al. | |

* cited by examiner

*Primary Examiner* — Linda Dvorak
*Assistant Examiner* — Brian M Antiskay
(74) *Attorney, Agent, or Firm* — Christopher & Weisberg, P.A.

(57) ABSTRACT

A catheter includes an outer jacket, a shaft member, a transition member and a core member. The outer jacket has a first interior passage at a proximal end and a second interior passage at a distal end. The shaft member is arranged within the outer jacket. The transition member is fixedly secured to the shaft member and includes a window. The core member is fixedly secured to the transition member. The window in the transition member allows communication between the first interior passage and the second interior passage.

15 Claims, 4 Drawing Sheets

CATHETER

CROSS-REFERENCE TO RELATED APPLICATION

This application claims the benefit of U.S. Provisional Application No. 61/169,263, filed on Apr. 14, 2009. The entire disclosure of the above application is incorporated herein by reference.

INTRODUCTION

The human anatomy includes many types of tissue that can either voluntarily or involuntarily, perform certain functions. However, after disease or injury, certain tissues may no longer operate within general anatomical norms. For example, after disease, injury, age, or combinations thereof, the heart muscle may begin to experience certain failures or deficiencies. In one example, the heart muscle may begin to develop an abnormal rhythm, which can be generally referred to as a cardiac arrhythmia.

Currently, many different devices and methods have been developed for both diagnosis and for treatment of the various symptoms of cardiac arrhythmias. In one example, in order to treat an abnormal heart rhythm involving the atria, or atrial fibrillation, devices and methods can be employed to electrically isolate a portion of the heart muscle from the atria, such as isolating one or more of the pulmonary veins from the left atrium. Prior to or after isolating one or more of the pulmonary veins, it may be desirable to determine the electrical activity within the heart muscle.

SUMMARY

The present disclosure relates to a mapping catheter utilized to determine the electrical conductivity of the heart muscle and, more specifically, to an improved mapping catheter construction that provides increased stiffness in the body of the catheter, and increased flexibility in the transition between the proximal portion (the shaft member) and the distal portion (core member) of the catheter.

In this regard, provided is a catheter that includes an outer jacket, a shaft member, a transition member and a core member. The outer jacket has a first interior passage at a proximal end and a second interior passage at a distal end. The shaft member is arranged within the outer jacket. The transition member is fixedly secured to the shaft member and includes at least one window. The core member is fixedly secured to the transition member. The at least one window in the transition member allows communication between the first interior passage and the second interior passage.

In further exemplary embodiments of the present disclosure, a catheter assembly is provided. The catheter assembly includes an outer jacket, a shaft member, a transition member, a plurality of electrical leads and a core member. The outer jacket has a first interior passage at a proximal end and a second interior passage at a distal end. The shaft member is arranged within the outer jacket. The transition member is fixedly secured to the shaft member and includes a plurality of windows that allows communication between the first interior passage and the second interior passage. The plurality of electrical leads extends from the proximal end to the distal end. The plurality of electrical leads extends from the first interior passage, through the plurality of windows and into the second interior passage. The core member is fixedly secured to the transition member.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
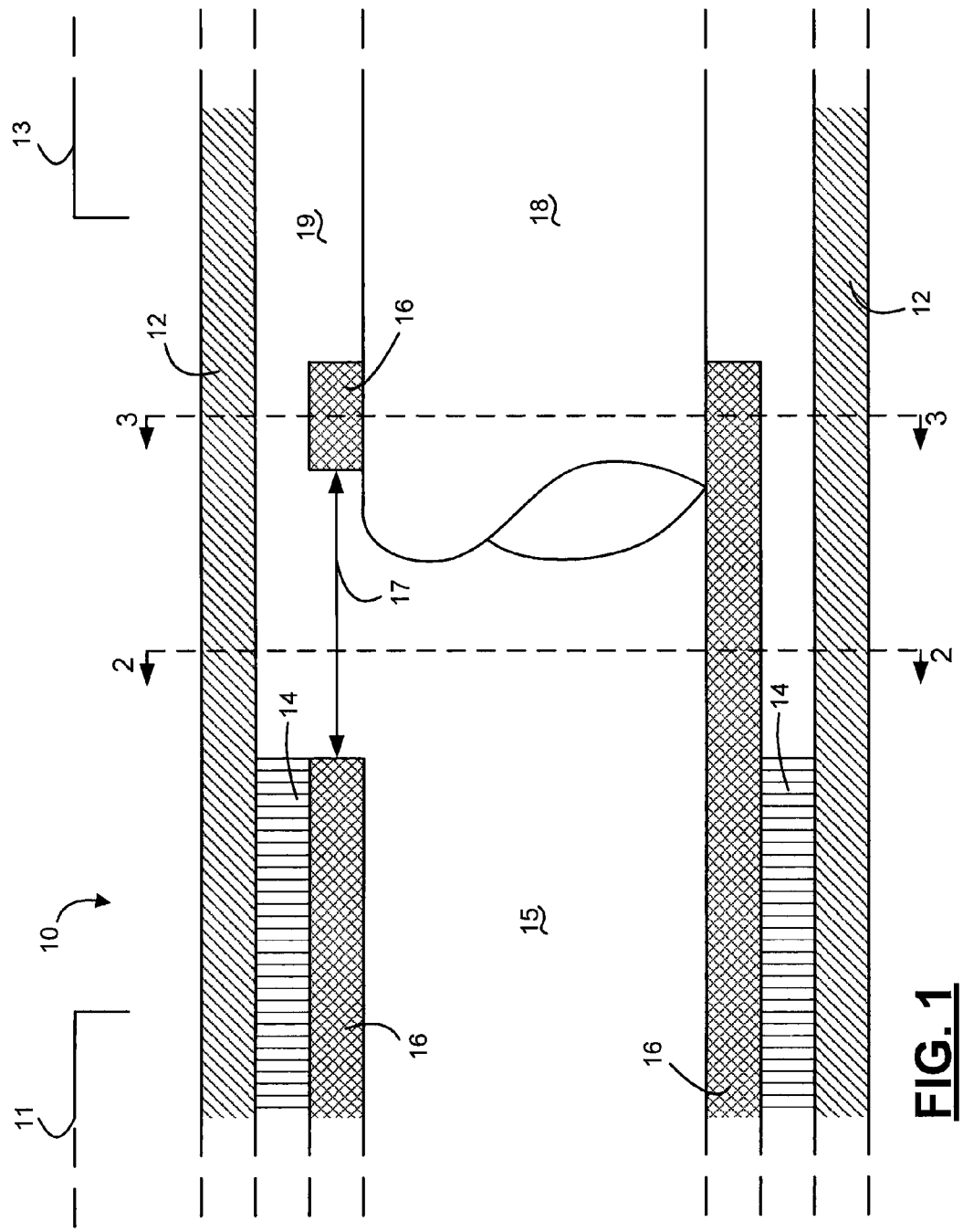
FIG. 1 is a longitudinal cut-away view of a catheter according to various embodiments of the present disclosure.

The following description is merely exemplary in nature and is not intended to limit the present disclosure, application, or uses. It should be understood that throughout the drawings, corresponding reference numerals indicate like or corresponding parts and features.

Furthermore, the teachings of the present disclosure can be utilized in conjunction with the systems and methods disclosed in co-pending U.S. patent application Ser. No. 11/021,113 (filed on Dec. 22, 2004), U.S. Ser. No. 12/199,016 (filed on Aug. 27, 2008) and U.S. Ser. No. 12/199,255 (filed on Aug. 27, 2008), which are herein incorporated by reference in their entirety.

Referring now to FIG. 1, a longitudinal cut-away view of an exemplary catheter 10 according to various embodiments of the present disclosure is illustrated. The illustrated catheter design can be utilized, for example, as the sensing guidewire disclosed in U.S. patent application Ser. Nos. 11/021,113; 12/199,016; and 12/199,255 referenced above. The catheter 10 includes a proximal end 11 and a distal end 13. In some embodiments, outer jacket 12 is a hollow tube structure and is arranged upon the exterior circumference of catheter 10. Outer jacket 12 can be formed of almost any biocompatible material, such as polyvinyl acetate or any biocompatible plastic or metal alloy. For example, the material marketed under the trade name Pebax® Polyether Block Amides sold by Arkema can be used to form outer jacket 12.

Arranged within outer jacket 12 is a shaft member 14. In some embodiments, shaft member 14 is a hollow tube structure that is present in the proximate section 11 and does not extend to the distal end 13 of the catheter 10. Shaft member 14 can be formed of almost any suitable material, such as a plastic or metal alloy. In various embodiments of the present disclosure, the shaft member 14 is a stainless steel hypotube, although other materials and constructions can be used, e.g., a braided composite material, a laminated composite material, an extruded composite material or a Nickel Titanium ("Nitinol") hypotube. Shaft member 14 can be slidably engaged with or bonded to the outer jacket 12.

According to various embodiments of the present disclosure, a transition member 16 is arranged within shaft member 14. Transition member 16 can be a hollow tube structure that is fixedly secured to shaft member 14. For example only, transition member 16 can have a longitudinal length of 1-2.5 centimeters and a diameter of 0.5-0.8 millimeters. Transition member 16 can be formed of almost any suitable material, such as a plastic or metal alloy. In various embodiments, transition member 16 can be formed of stainless steel or Nitinol. Transition member 16 can be fixedly secured to shaft member 14, for example, by adhesive, welding or crimping. For example only, if the shaft member 14 and transition member 16 are both formed of stainless steel, the shaft member 14 and transition member 16 can be bonded by welding. Alternatively, if the shaft member 14 is formed of stainless steel and the transition member 16 is formed of Nitinol, the shaft member 14 and transition member 16 can be bonded by crimping.

Arranged partially within transition member 16 is core member 18. Core member 18 can be a solid cylindrical wire, e.g., formed of Nitinol, stainless steel or other suitable material. Core member 18 provides increased stiffness and can be utilized to navigate the distal end 13 of the catheter 10. Core member 18 is fixedly secured to one end of the transition member 16. For example only, if the transition member 16 and core member 18 are both formed of Nitinol, the transition member 16 and core member 18 can be bonded by welding. Alternatively, if the transition member 16 is formed of stainless steel and the core member 18 is formed of Nitinol, the transition member 16 and core member 18 can be bonded by crimping.

Figure 2:
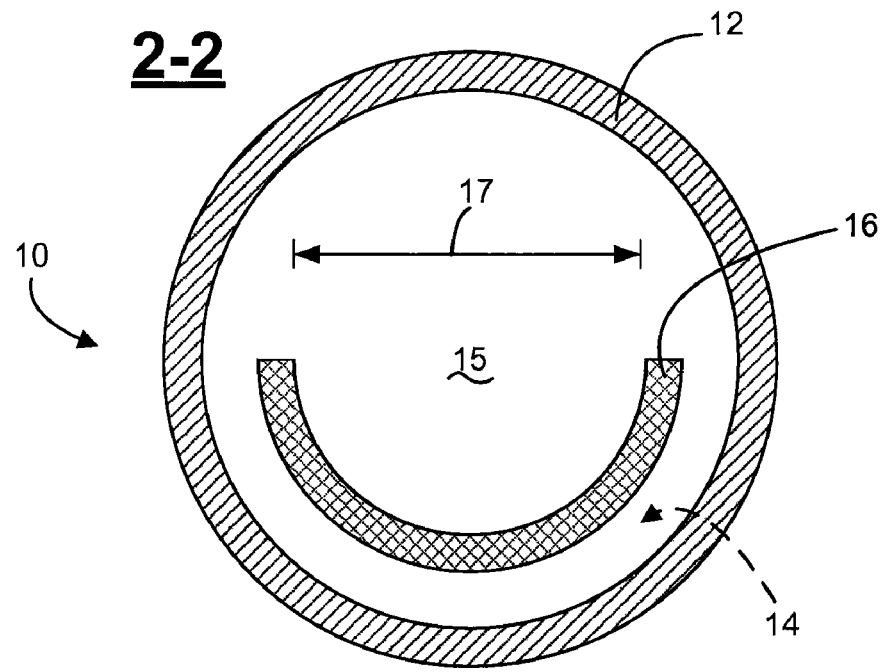
FIG. 2 is a cross-sectional view of the catheter of FIG. 1 taken along line 2-2.

Transition member 16 provides for the coupling of shaft member 14 with core member 18. An opening or "window" 17 can be formed at the distal end of transition member 16 to allow communication between the interior passage 15 at proximal end 11 and interior passage 19 at distal end 13. The interior passages 15, 19 can, for example, carry electrical leads (not shown) from proximal end 11 to distal end 13. Accordingly, window 17 provides an opening to allow the electrical leads to extend between interior passages 15, 19. Window 17 is sized to accommodate the electrical leads, while also reducing the sensitivity of catheter 10 to bend and/or kink when advanced within a body lumen. For example only, window 17 can have a longitudinal length of 2-5 millimeters. Furthermore, the window 17 can be sized to extend 180° degrees of the circumference of the transition member 16 (as shown in FIG. 2), or any other circumferential distance. In various embodiments, the window 17 is symmetrical about the center axis of the catheter 10 in order to minimize the bending bias at the interface between transition member 16 and core member 18.

A cross-sectional view of the catheter 10 of FIG. 1 taken along line 2-2 is illustrated in FIG. 2. This cross-section is taken at the point along the length of catheter 10 that corresponds to the location of window 17. The outer jacket 12 is shown as having a circular cross-section, although other shapes are within the scope of the present disclosure. The location of shaft member 14 is shown, although shaft member 14 is not explicitly illustrated. Transition member 16 is shown as having the shape of a half-circle, as window 17 is shown to extend 180° degrees of the circumference of the transition member 16, as described above. Interior passage 15 is located within the outer jacket, shaft member 14, and transition member 16.

Figure 3:
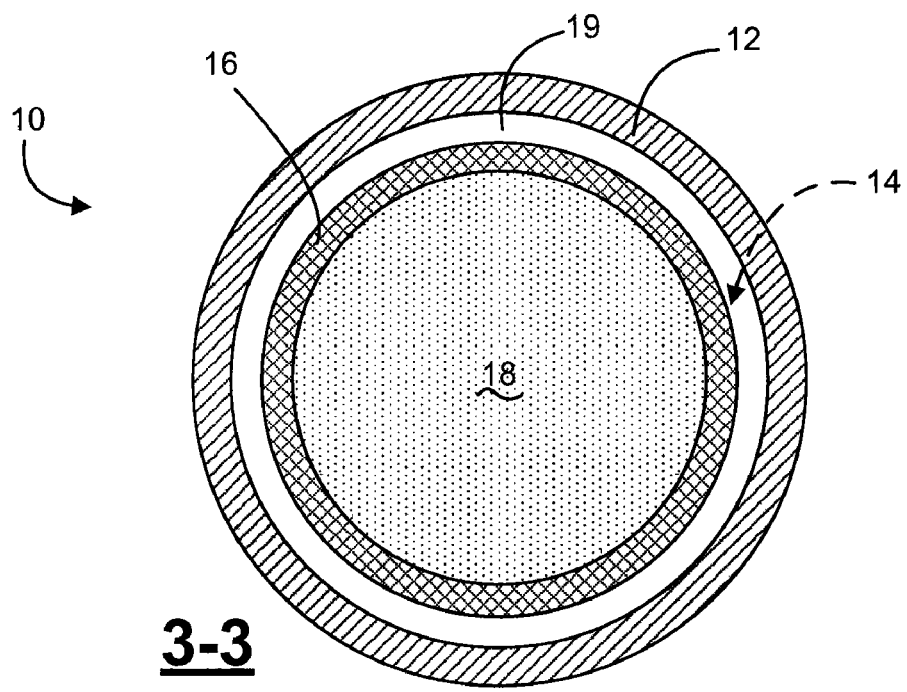
FIG. 3 is a cross-sectional view of the catheter of FIG. 1 taken along line 3-3.

A cross-sectional view of the catheter 10 of FIG. 1 taken along line 3-3 is illustrated in FIG. 3. This cross-section is taken at the point along the length of catheter 10 that corresponds to the location where core member 18 is fixedly secured to transition member 16, which is distal to window 17. Similar to FIG. 2 above, the location of shaft member 14 is shown even though shaft member 14 is not explicitly illustrated. Interior passage 19 is located between transition member 16 and outer jacket 12.

Figure 4:
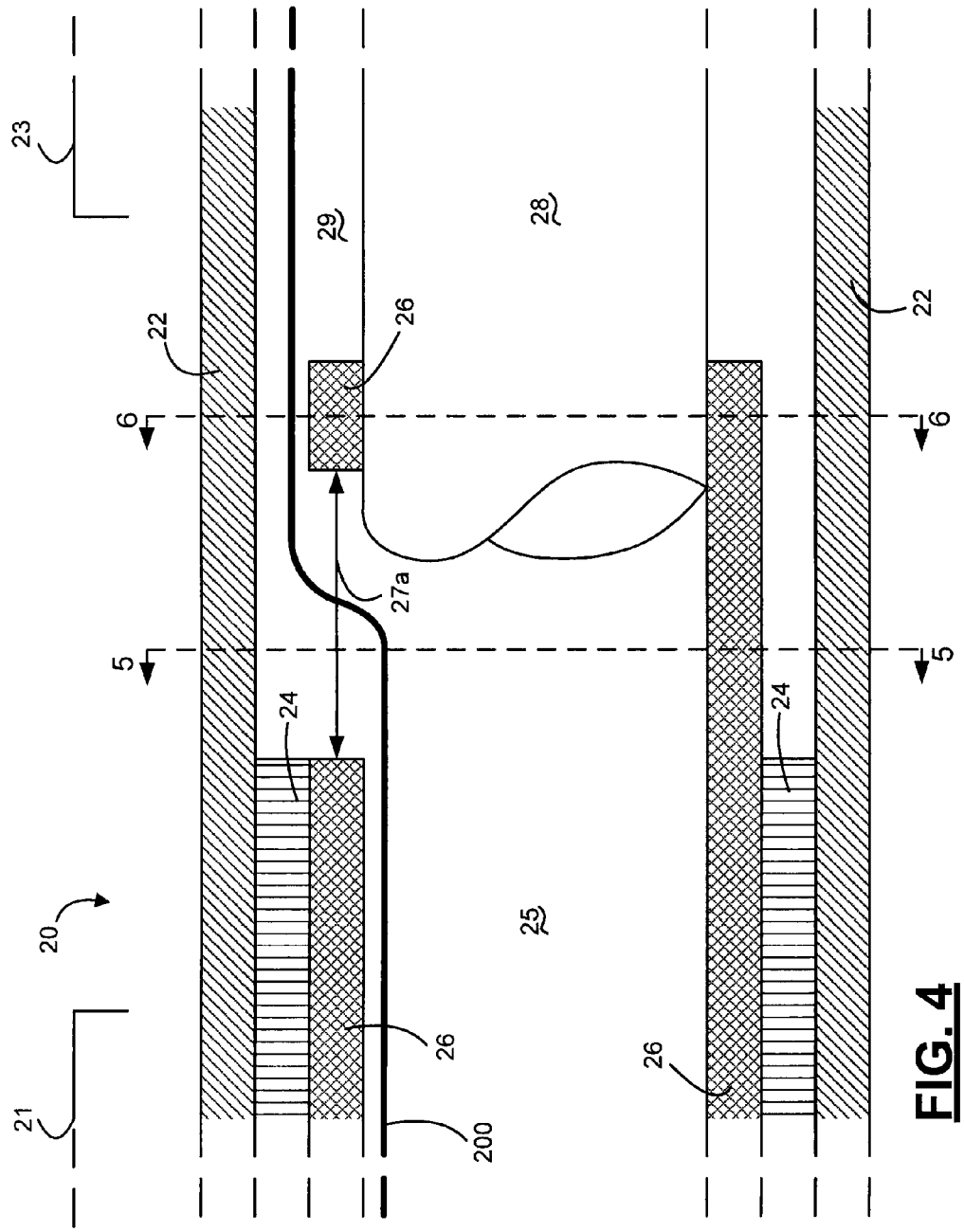
FIG. 4 is a longitudinal cut-away view of a catheter according to various embodiments of the present disclosure.

Referring now to FIG. 4, a longitudinal cut-away view of an exemplary catheter 20 according to various embodiments of the present disclosure is illustrated. Catheter 20 is of a similar construction to catheter 10 illustrated in FIGS. 1-3. The illustrated catheter design can be utilized, for example, as the sensing guidewire disclosed in U.S. patent application Ser. Nos. 11/021,113; 12/199,016; and 12/199,255 referenced above. The catheter 20 includes a proximal end 21 and a distal end 23. In some embodiments, outer jacket 22 is a hollow tube structure and is arranged upon the exterior circumference of catheter 20. Outer jacket 22 can be formed of almost any biocompatible material, such as polyvinyl acetate or any biocompatible plastic or metal alloy. For example, the material marketed under the trade name Pebax® Polyether Block Amides sold by Arkema can be used to form outer jacket 22.

Arranged within outer jacket 22 is a shaft member 24. In some embodiments, shaft member 24 is a hollow tube structure that is present in the proximate section 21 and does not extend to the distal end 23 of the catheter 20. Shaft member 24 can be formed of almost any suitable material, such as a plastic or metal alloy. In various embodiments of the present disclosure, the shaft member 24 is a stainless steel hypotube, although other materials and constructions can be used, e.g., a braided composite, a laminated extruded structure or a Nickel Titanium ("Nitinol") hypotube. Shaft member 24 can be slidably engaged with or bonded to the outer jacket 22.

According to various embodiments of the present disclosure, a transition member 26 is arranged within shaft member 24. Transition member 26 can be a hollow tube structure that is fixedly secured to shaft member 24. For example only, transition member 26 can have a longitudinal length of 1-2.5 centimeters and a diameter of 0.5-0.8 millimeters. Transition member 26 can be formed of almost any suitable material, such as a plastic or metal alloy. In various embodiments, transition member 26 can be formed of stainless steel or Nitinol. Transition member 26 can be fixedly secured to shaft member 24, for example, by adhesive, welding or crimping. For example only, if the shaft member 24 and transition member 26 are both formed of stainless steel, the shaft member 24 and transition member 26 can be bonded by welding. Alternatively, if the shaft member 24 is formed of stainless steel and the transition member 26 is formed of Nitinol, the shaft member 24 and transition member 26 can be bonded by crimping.

Arranged partially within transition member 26 is core member 28. Core member 28 can be a solid cylindrical wire, e.g., formed of Nitinol, stainless steel or other suitable material. Core member 28 provides increased stiffness and can be utilized to navigate the distal end 23 of the catheter 20. Core member 28 is fixedly secured to one end of the transition member 26. For example only, if the transition member 26 and core member 28 are both formed of Nitinol, the transition member 26 and core member 28 can be bonded by welding. Alternatively, if the transition member 26 is formed of stainless steel and the core member 28 is formed of Nitinol, the transition member 26 and core member 28 can be bonded by crimping.

Transition member 26 provides for the coupling of shaft member 24 with core member 28. Three openings or "windows" (27a, 27b and 27c) can be formed at the distal end of transition member 26 to allow communication between the interior passage 25 at proximal end 21 and interior passage 29 at distal end 23. The interior passages 25, 29 can, for example, carry one or more electrical leads 200 from proximal end 21 to distal end 23. Accordingly, windows 27a-27c provide openings to allow the electrical leads 200 to extend between interior passages 25, 29. Each of the windows 27a-27c is sized to accommodate one or more of the electrical leads 200, while also reducing the sensitivity of catheter 20 to bend and/or kink when advanced within a body lumen. For example only, each window 27 can have a longitudinal length of 2-5 millimeters.

The use of multiple windows 27 provides for increased stiffness of the transition member 26 as opposed to the single window embodiments described above. In various embodiments, the windows 27 are evenly distributed along the circumference of transition member 26 such that the angles between midpoints of adjacent windows are approximately equal (for example, with three windows 27a-27c, the midpoints between adjacent windows are approximately 120° degrees apart).

Figure 5:
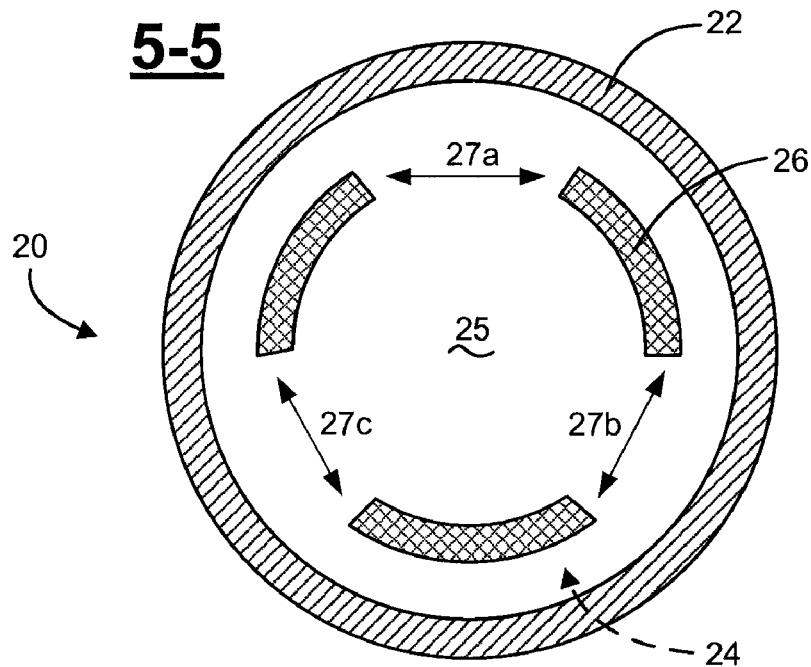
FIG. 5 is a cross-sectional view of the catheter of FIG. 4 taken along line 5-5.

A cross-sectional view of the catheter 20 of FIG. 4 taken along line 5-5 is illustrated in FIG. 5. This cross-section is taken at the point along the length of catheter 20 that corresponds to the location of windows 27a-27c. The outer jacket 22 is shown as having a circular cross-section, although other shapes are within the scope of the present disclosure. The location of shaft member 24 is shown, although shaft member 24 is not explicitly illustrated. Transition member 26 is shown as including windows 27a, 27b and 27c evenly distributed along the circumference of transition member 26. Interior passage 25 is located within the outer jacket, shaft member 24, and transition member 26.

Figure 6:
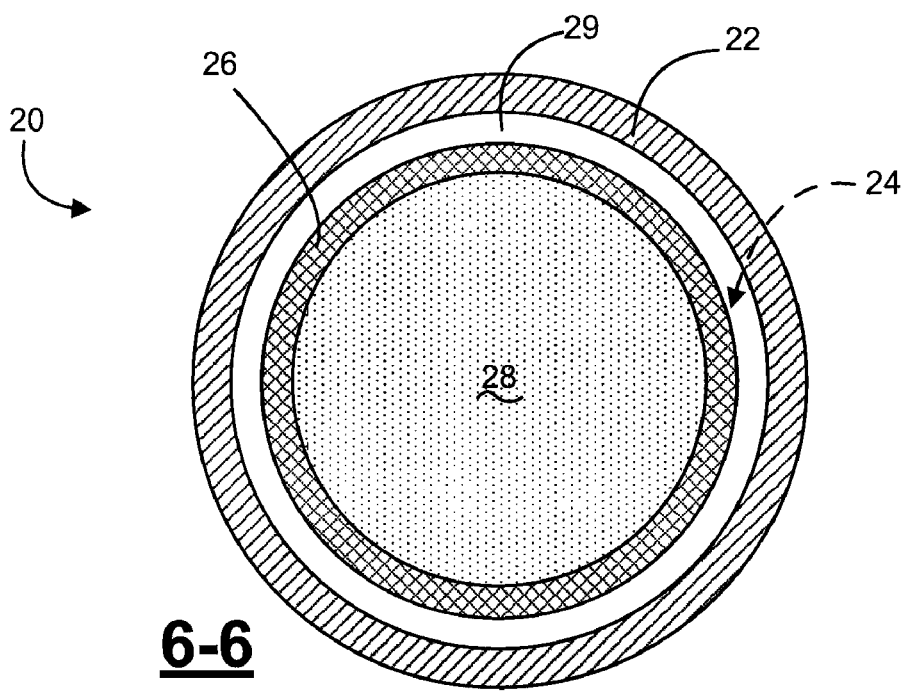
FIG. 6 is a cross-sectional view of the catheter of FIG. 4 taken along line 6-6.

A cross-sectional view of the catheter 20 of FIG. 4 taken along line 6-6 is illustrated in FIG. 6. This cross-section is taken at the point along the length of catheter 20 that corresponds to the location where core member 28 is fixedly secured to transition member 26, which is distal to windows 27. Similar to FIG. 5 above, the location of shaft member 24 is shown even though shaft member 24 is not explicitly illustrated. Interior passage 29 is located between transition member 26 and outer jacket 22.

The above described catheters 10, 20 have numerous advantages over prior art catheter designs. For example, catheters 10, 20 have increased integrity, robustness and ease of manufacture since an adhesive is not used to couple the core member to shaft member directly. Furthermore, the use of a transition member 16, 26 with one or more windows 17, 27 allows for the unobstructed passage of electrical leads or other elements through the full length of catheters 10, 20 without increasing the diameter of the catheter 10, 20. There is also an increase in the flexibility of the section of the catheter in which the shaft member 14, 24 is coupled to the core member 18, 28. Further advantages of the present disclosure will be apparent to those of ordinary skill in the art.

While specific examples have been described in the specification and illustrated in the drawings, it will be understood by those of ordinary skill in the art that various changes can be made and equivalents can be substituted for elements thereof without departing from the scope of the present disclosure. Furthermore, the mixing and matching of features, elements and/or functions between various examples is expressly contemplated herein so that one of ordinary skill in the art would appreciate from this disclosure that features, elements and/or functions of one example can be incorporated into another example as appropriate, unless described otherwise, above. Moreover, many modifications can be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this disclosure, but that the scope of the present disclosure will include any embodiments falling within the foregoing description.

What is claimed is:

1. A catheter, comprising:
   an outer jacket having a first interior passage at a proximal end and a second interior passage at a distal end;
   a shaft member arranged within the outer jacket;
   a transition member fixedly secured to the shaft member and defining at least one window; and
   a core member fixedly secured to the transition member, wherein the at least one window allows communication between the first interior passage and the second interior passage.

2. The catheter of claim 1, further comprising a plurality of electrical leads extending from the proximal end to the distal end.

3. The catheter of claim 2, wherein the plurality of electrical leads extend from the first interior passage, through the at least one window into the second interior passage.

4. The catheter of claim 1, wherein the transition member defines three windows.

5. The catheter of claim 4, wherein the three windows are evenly distributed along a circumference of the transition member.

6. The catheter of claim 4, further comprising a plurality of electrical leads extending from the proximal end to the distal end.

7. The catheter of claim 6, wherein each of the plurality of electrical leads extend from the first interior passage, through one of the three windows into the second interior passage.

8. The catheter of claim 7, wherein the three windows are evenly distributed along a circumference of the transition member.

9. The catheter of claim 1, wherein the core member is formed of Nickel Titanium, stainless steel or a combination thereof.

10. The catheter of claim 1, wherein the transition member is formed of Nickel Titanium, stainless steel or a combination thereof.

11. The catheter of claim 1, wherein the shaft member is formed of Nickel Titanium, stainless steel, a braided composite material, a laminated composite material, an extruded composite material or a combination thereof.

12. The catheter of claim 1, wherein the outer jacket is formed of polyvinyl acetate, a biocompatible plastic or metal alloy or a combination thereof.

13. The catheter of claim 1, wherein the transition member has a diameter between 0.5-0.8 millimeters.

14. A catheter assembly, comprising:
   an outer jacket having a first interior passage at a proximal end and a second interior passage at a distal end;
   a shaft member arranged within the outer jacket;
   a transition member fixedly secured to the shaft member and defining a plurality of windows, wherein the plurality of windows allows communication between the first interior passage and the second interior passage;
   a plurality of electrical leads extending from the proximal end to the distal end, the plurality of electrical leads extending from the first interior passage, through the plurality of windows into the second interior passage; and
   a core member fixedly secured to the transition member.

15. The catheter assembly of claim 14, wherein the plurality of windows is evenly distributed along a circumference of the transition member.

* * * * *